United States Patent
Sanders et al.

[11] Patent Number: 5,099,058
[45] Date of Patent: Mar. 24, 1992

[54] N,N-DISUBSTITUTED OLIGOURETHANES AND POLYURETHANES, A PROCESS FOR THEIR PREPARATION, AND THEIR USE IN THE PRODUCTION OF PLASTICS

[76] Inventors: Josef Sanders, c/o Mobay Corporation, Mobay Rd., Pittsburgh, Pa. 15205; Dieter Dieterich, Bayer Aktiengesellschaft, D 5090 Leverkusen Bayerwerk, Fed. Rep. of Germany

[21] Appl. No.: 501,212

[22] Filed: Mar. 29, 1990

Related U.S. Application Data

[63] Continuation-in-part of Ser. No. 379,522, Jul. 13, 1989, abandoned.

Foreign Application Priority Data

Jul. 5, 1989 [EP] European Pat. Off. ...... 89 112 244.2

[51] Int. Cl.$^5$ .................. C07C 261/02; C07C 69/96; C07F 7/10
[52] U.S. Cl. ........................ 560/26; 560/158; 560/160; 560/148; 560/115; 556/420; 556/421; 558/276
[58] Field of Search ........... 560/26, 158, 160, 8, 560/148, 115; 556/420, 421; 558/276

[56] References Cited

U.S. PATENT DOCUMENTS

| | | | |
|---|---|---|---|
| 3,397,184 | 8/1968 | Heydkemp et al. | 560/160 |
| 3,459,789 | 8/1969 | Müller et al. | 560/160 |
| 4,413,112 | 11/1983 | Reiff | 528/73 |
| 4,472,550 | 9/1984 | Reiff et al. | 524/589 |

FOREIGN PATENT DOCUMENTS

| | | |
|---|---|---|
| 1204547 | 5/1986 | Canada . |
| 1116783 | 6/1968 | United Kingdom . |
| 1121265 | 7/1968 | United Kingdom . |
| 1324527 | 7/1973 | United Kingdom . |

Primary Examiner—John Kight, III
Assistant Examiner—John M. Cooney, Jr.

[57] ABSTRACT

The present invention relates to N,N-disubstituted compounds containing urethane groups and terminal hydroxyl groups corresponding to the general formula

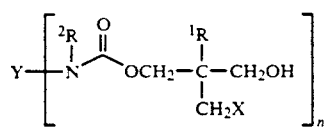

wherein
X is the residue of a strong memobasic or polybasic acid remaining after dissociation of the proton or protons of said acid or a hydroxyl group;
Y is an n-functional hydrocarbon group having a molecular weight of from about 15 to about 8000 (preferably from about 300 to about 4000) and optionally interrupted by oxygen, sulfur, or silicon atoms, or by ester, carbonate, urea, N-monosubstituted urethane, or N,N-disubstituted urethane groups;
$1_R$ hydrogen or a hydrocarbon group having a molecular weight of from about 15 to about 200;
$2_R$ is the radical of an alkylating or arylating agent; and is an integer of from 2 to about 6.

The present invention further relates to a process for preparing such compounds and to a method for using such compounds in the production of plastics.

29 Claims, No Drawings

N,N-DISUBSTITUTED OLIGOURETHANES AND POLYURETHANES, A PROCESS FOR THEIR PREPARATION, AND THEIR USE IN THE PRODUCTION OF PLASTICS

This application is a continuation-in-part of application Ser. No. 07/379,522, filed Jul. 13, 1989.

BACKGROUND OF THE INVENTION

This invention relates to new hydroxyl-terminated N,N-disubstituted oligourethanes and polyurethanes, to a process for their preparation, and to their use in the production of plastics.

N,N-Disubstituted urethanes are known to show greater thermal stability and resistance to hydrolysis than N-mono-substituted urethanes. Since N,N-disubstituted urethanes cannot be obtained by polyaddition of diols to diisocyanates, they are generally produced by polycondensation of bischlorocarbonic acid esters with disecondary amines in the presence of bases. See Houben-Weyl, Vol. E20, Part 2, Thieme-Verlag, Stuttgart, pages 1580, 1710. Disadvantages of this process include the limited availability and the comparatively high price of the disecondary amines, as well as the poor reproducibility in obtaining the average molecular weights required. In addition, this process yields only amino-terminated products that for many applications have undesirably high reactivity with isocyanates. Accordingly, there has until now been little technical interest in N,N-di-substituted urethanes.

The object of the present invention is to develop an economic process for the production of N,N-disubstituted urethanes which avoids the described disadvantages.

It has now been found that hydroxyl-terminated N,N-disubstituted polyurethanes can be produced by reaction of isocyanate-terminated compounds with oxetane methanols optionally substituted in the 3-position; complete or partial alkylation of the resulting urethane- and oxetane-group-containing compounds at the urethane nitrogens by the reaction with alkylating agents in the presence of metal hydroxides; and, finally, formation of terminal hydroxyl groups by exposing the oxetane groups to strong acid to induce ring opening. The resultant urethane-containing compounds, because of the multiplicity of hydroxyl groups, are useful as chain extenders or crosslinking agents in the preparation of polyurethanes and other isocyanate-based plastics.

U.S. Pat. No. 4,413,112 and 4,472,550 disclose certain oxetane-containing urethanes used as emulsifiers in the production of molded articles containing lignocellulose. The disclosed compounds include only linearly extended structures and not the branched structures of the present invention.

British Patent 1,324,527 discloses certain compounds having the general formula

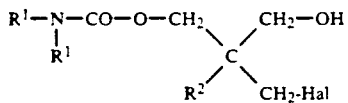

wherein $R^1$ can be, inter alia, various hydrocarbon groups; $R^2$ can be, inter alia, various hydrocarbon groups or $CH_2$—OH; and Hal is a halogen. The group $R^1$, however, is never described as a multivalent group having more than one substituent, as is required for the present invention. Consequently, compounds of the reference in which $R^2$ is a hydrocarbon group cannot serve as chain extenders or crosslinkers because such compounds have only one hydroxyl group. Compounds of the reference in which $R^2$ is $CH_2$—OH have two proximately located hydroxyl groups and can thus serve as chain extenders, but, because the $R^1$ group is never multivalent, such compounds never have distally located hydroxyl groups and must, therefore, be inherently different chain extenders from the compounds of the present invention.

The British Patent discloses a process for preparing the disclosed compounds by ring-opening an oxetane-ring precursor using a method similar to that used in the present invention. Unlike the present invention, however, the reference does not disclose or suggest how N,N-disubstituted urethane embodiments could be prepared. It has now surprisingly been found that the N-alkylation or N-arylation of oxetane-containing N-monosubstituted urethane intermediates occur smoothly without significantly cleaving the urethane ester bond or ring-opening the oexetane ring.

SUMMARY OF THE INVENTION

The present invention relates to new N,N-disubstituted compounds containing urethane groups and terminal hydroxyl groups corresponding to the following general formula

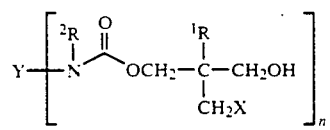

wherein

X is the residue of a strong monobasic or polybasic acid remaining after dissociation of the proton or protons of said acid (preferably a chlorine, bromine, or iodine atom) or a hydroxyl group;

Y is an n-functional (preferably difunctional) hydrocarbon group having a molecular weight of from about 15 to about 8000 (preferably from about 300 to about 4000) and optionally interrupted by oxygen, sulfur, or silicon atoms, or by ester, carbonate, urea, N-monosubstituted urethane, or N,N-disubstituted urethane groups;

$^1R$ is hydrogen or a hydrocarbon group having a molecular weight of from about 15 to about 200 (preferably methyl or ethyl);

$^2R$ is the radical of an alkylating or arylating agent (preferably methyl, ethyl, or benzyl); and n is an integer of from 2 to about 6 (preferably 2).

The present invention also relates to a process for the production of N,N-disubstituted compounds of the invention containing urethane groups and terminal hydroxyl groups, as well as to related "monomeric compounds in which n is 1. The process of the invention comprises (a) reacting (i) n-functional isocyanate-terminated compounds of the general formula Z(NCO)

with (ii) oxetane methanols of the general formula

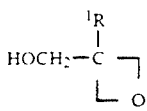

to form oxetane-terminated compounds of the general formula

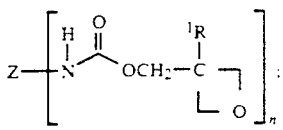

(b) reacting the oxetane-terminated compounds obtained in (a) with (iii) alkylating or arylating agents in the presence of metal hydroxides to form compounds of the general formula

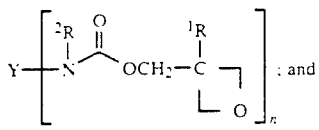
and (c) reacting the compounds obtained in (b) with strong acids to form hydroxyl-terminated compounds of the general formula

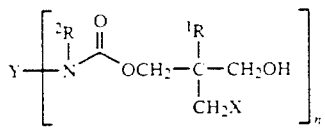

wherein X, Y, $^1R$, and $^2R$, are defined as above, r is from 1 to about 6, and Z is an n-functional (preferably difunctional) hydrocarbon group having a molecular weight of from about 15 to about 8000 (preferably from about 300 to about 4000) and optionally interrupted by oxygen, sulfur, or silicon atoms, or by ester, carbonate, urea, or N-monosubstituted urethane groups. The relationship of Z to Y is dependent upon the reactivity of the moiety Z to alkylating or arylating agents according to principles easily understood by one skilled in the art. That is, Y and Z may be, but are not necessarily, identical.

The present invention also relates to the use of the hydroxyl-terminated N,N-disubstituted compounds obtained as described above in the production of plastics, particularly polyurethane plastics, by the isocyanate polyaddition process.

DETAILED DESCRIPTION OF THE INVENTION

Suitable starting materials (i) for the production of compounds according to the process of the invention include isocyanates corresponding to the general formula $$Z(NCO)_n$$

in which Z is defined as above and n is from 1 to about 6. Compounds according to the invention, of course, are prepared from isocyanates for which n is from 2 to about 6. Suitable isocyanates of this type are, for example, aliphatic, araliphatic, and aromatic mono- and polyisocyanates of the type described, for example, in Ullmann's *Encyklopädie der technischen Chemie*, 4th Edition, Vol. 19, pages 303-304. Examples of suitable isocyanates include ethyl, propyl, butyl, pentyl, and hexyl isocyanates; 6-chlorohexyl isocyanate; cyclohexyl isocyanate; benzyl isocyanate; tetramethylene, hexamethylene, and decamethylene diisocyanates; 1,3-di(3-isocyanatopropoxy)-2,2-dimethylpropane; cyclohexane-1,4-diisocyanate, methylcyclohexane-2,4-diisocyanate, methylcyclohexane-2,6-diisocyanate, cyclohexane-1,3-diisocyanate, and mixtures of methylcyclohexane-2,4-diisocyanate and methylcyclohexane-2,6-diisocyanate; dicyclohexylmethane -4,4'-diisocyanate; 1-isocyanato-3-isocyanatomethyl -3,5,5-trimethylcyclohexane (isophorone diisocyanate); 1,2-di(isocyanatomethyl)cyclo-butane; m- and p-xylylene diisocyanate and $\alpha,\alpha,\alpha',\alpha'$-tetramethyl-m- and -p-xylylene diisocyanate; hexahydroxylylene diisocyanate; phenyl isocyanate; toluene isocyanate; 1,3- and 1,4-phenylene diisocyanate, 2,4- and 2,6-tolylene diisocyanate, and mixtures of these isomers; diphenylmethane -2,4'- and -4,4'-diisocyanate; 1,5- and 2,4-naphthylene diisocyanate; alkylbenzene diisocyanates according to EP 058,368; triphenylmethane-4,4',4"-triisocyanate; polyphenyl polymethylene polyisocyanates of the type obtained by phosgenation of aniline-formaldehyde condensates and described, for example, in British Patents 874,430 and 848,671; m- and p-isocyanatophenylsulfonyl isocyznates according to U.S. Pat. No. 3,454,606; perchlorinated aryl polyisocyanates of the type described, for example, in German Auslegeschrift 1,157,601 (believed to correspond to U.S. Pat. No. 3,277,138); polyisocyanates containing carbodiimide groups of the type described in German Patentschrift 1,092,007 (believed to correspond to U.S. Pat. No. 3,152,162); diisocyanates of the type described in U.S. Pat. No. 3,492,330; polyisocyanates containing allophanate groups of the type described in British Patent 994,890, Belgian Patent 761,626, and published Dutch patent application 7,102,524; polyisocyanates containing isocyanurate groups of the type described, for example, in U.S. Pat. No. 3,001,973, German Patentschriften 1,002,789, 1,222,067, and 1,027,394, and in German Offenlegungsschrifts 1,929,034 and 200,048; polyisocyanates containing urethane groups of the type described, for example, in Belgian Patent 752 261 and U.S. Pat. No. 3,394,164; polyisocyanates containing acylated urea groups according to German Patentschrift 1,230,778; polyisocyanates containing biuret groups of the type described, for example, in German Patentschrift 1,101,394 (believed to correspond to U.S. Pat. Nos. 3,124,605 and 3,201,372) and British Patent 889,050; polyisocyanates produced by telomerization reactions of the type described, for example, in U.S. Pat. No. 3,654,106; polyisocyanates containing ester groups of the type described, for example, in British Patents 965,474 and 1,072,956, U.S. Pat. No. 3,567,763, and German Patentschrift 1,231,688; reaction products of the above-mentioned isocyanates with acetals according to German Patentschrift 1,072,385; and polyisocyanates containing polymeric fatty acid residues according to U.S. Pat. No. 3,455,883. It is also possible to use the distillation residues containing isocyanate groups obtained in the commercial production of isocyanates, optionally in solution in one or more of the above-mentioned polyisocyanates. It is also possible to use mixtures of the above-mentioned polyisocyanates.

Other suitable isocyanates (i) are so-called isocyanate prepolymers obtainable by methods known in the art, such as, for example, polyaddition of polyamines, polyhydroxyl compounds, or, less preferably, polythiols with excess quantities of polyisocyanates. The average molecular weight of the isocyanate prepolymers may be varied within wide limits depending on the ratio of NCO groups to NH, OH or SH groups. See D. Dieterich, *Angewandte Macromolekulare Chemie* 1979, 76/77, 1114, pages 79 to 107. Polyfunctional (preferably difunctional) aliphatic, araliphatic, and aromatic isocyanates of the type already mentioned above are suitable for the production of the NCO prepolymers.

Suitable polyamines which may be reacted with the diisocyanates to form prepolymers include, for example, ethylenediamine, 1,4-tetramethylenediamine, 1,11-undecanemethylenediamine, 1,12-dodecamethylenediamine and mixtures thereof; 1-amino-3,3,5-trimethyl-5-amino-methylcyclohexane ("isophoronediamine"); 2,4- and 2,6-hexahydrotolylenediamine and mixtures thereof; perhydro-2,4'- and -4,4'-diaminodiphenylmethane; p-xylylenediamine; bis(3-aminopropyl)meihylamine; diaminoperhydroanthracenes (German Offenlegungsschrift 2,638,731); and cycloaliphatic triamines according to German Offenlegunsschrift 2,614,244. Also suitable for use in accordance with the invention are hydrazine and substituted hydrazines, such as methylhydrazine, N,N'-dimethylhydrazine, and homologs thereof; acid dihydrazides such as carbodihydrazide, oxalic acid dihydrazide, the dihydrazides of malonic acid, succinic acid, glutaric acid, adipic acid, 8-methyl adipic acid, sebacic acid, hydracrylic acid, and terephthalic acid; semicarbazidoalkylene hydrazides such as 8-semicarbazidopropionic acid hydrazide (German Offenlegungsschrift 1,770,591); semicarbazidoalkylene carbazinic esters such as 2-semicarbazido-ethyl carbazinic ester (German Offenlegungsschrift 1,918,504); and aminosemicarbazide compounds such as 8-aminoethyl-semicarbazidocarbonate (German Offenlegungsschrift 1,902,931). To control their reactivity, the amino groups may be completely or partly blocked by aldimine or ketimine groups (U.S. Patent No. 3,734,894;-German Offenlegungsschriit 2,637,115).

Suitable aromatic diamines for use in preparing prepolymers include bisanthranilic acid esters according to German Offenlegungsschriften 2,040,644 and 2,160,590; 3,5- and 2,4-diaminobenzoic acid esters according to German Offenlegungsschrift 2,025,900; diamines containing ester groups described in German Offenlegungsschriften 1,803,635 (believed to be equivalent to U.S. Pat. Nos. 3,681,290 and 3,736,250), 2,040,650, and 2,160,589; diamines containing ether groups according to German Offenlegungsschriften 1,770,525 and 1,809,172 (U.S. Pat. Nos. 3,654,364 and 3,736,295), 2-halogen-1,3-phenylenediamines optionally substituted in the 5-position (German Offenlegungsschriften 2,001,772, 2,025,896, and 2,065,869); 3,3'-dichloro-4,4'-diaminodipherylmethane; tolylenediamine; 4,4'-diaminodiphenylmethane 4,4'-diaminodiphenyl disulfides (German Offenlegungsschrift 2,404,976); diaminodiphenyl dithioethers (German Offenlegungsschrift 2,509,404); aromatic diamines substituted by alkylthio groups (German Offenlegungsschrift 2,638,760); diaminobenzene phosphoric acid esters (German Offenlegungsschriit 2,459,491); aromatic diamines containing sulfonate or carboxylate groups (German Offenlegungsschrift 2,720,166); and high-melting diamines mentioned in German Offenlegungsschrift 2,635,400. Examples of aliphaticaromatic diamines include aminoalkylthioanilines according to German Offenlegungsschrift 2,734,574.

Suitable polyhydroxyl compounds for the production of the isocyanate prepolymers include, preferably, diols having an average molecular weight of from about 60 to about 3000 (more preferably from about 60 to about 1000) and low molecular weight polyols. Examples of such polyhydroxyl compounds include ethylene glycol, 1,2- and 1,3-propylene glycol, 1,4- and 2,3-butylene glycol, pentane-1,5-diol, hexane-1,6-diol, octane-1,8-diol, neopentyl glycol, 1,4-bis(hydroxymethyl)cyclohexane, 2-methylpropane-1,3-diol, dibromobutenediol (U.S. Pat. No. 3,723,392), glycerol, trimethylolpropane, 1, 2,6-hexanetriol, trimethylolethane, pentaerythritol, quiniiol, mannitol and sorbitol, castor oil, diethylene glycol, triethylene glycol, tetraethylene glycol, higher polyethylene glycols having a molecular weight of up to about 400, dipropylene glycol, higher polypropylene glycols having a molecular weight of up to about 400, dibutylene glycol, higher polybutylene glycols having a molecular weight of up to about 400, 4,4'-dihydroxydiphenylpropane, dihydroxymethyl hydroquinone, ethanolamine, diethanolamine, N-methyldiethanolamine, triethanolamine, and 3-aminopropanol.

Other suitable low molecular weight polyols according to the invention include mixtures of hydroxy aldehydes and hydroxy ketones ("formose") and the polyhydric alcohols ("formitol") obtained therefrom by reduction, of the type formed in the autocondensation of formaldehyde hydrate in the presence of metal compounds as catalysts and in the presence of compounds capable of enediol formation as co-catalysts (German Offenlegungsschriften 2,639,084, 2,714,104, 2,721,186, 2,738,154, and 2,738,512). To obtain plastics showing improved flame resistance, these formoses are advantageously used in combination with aminoplast formers and/or phosphites (German Offenlegungsschriften 2,738,513 and 2,738,532). Solutions of polyisocyanate polyaddition products, particularly polyurethane ureas containing ionic groups and/or polyhydrazocicarbonamides, in low molecular weight polyhydric alcohols may also be used as the polyol component in accordance with the invention (German Offenlegungsschrift 2,638,759).

Other suitable polyhydroxyl compounds for the production of isocyanate prepolymers include relatively high molecular weight compounds having an average molecular weight of from 400 to 3000 (preferably from 400 to 1000) and containing at least 2 to 6 (preferably 2) hydroxyl groups per molecule. For example, it is possible to use polyacetals, polythioethers, polycarbonates, polyamides, polysiloxanes, polybutadienes, polyesters, polylactones, and polyethers containing hydroxyl groups normally used in polyurethane chemistry. Especially preferred are polyethers containing hydroxyl groups.

Suitable polyethers containing hydroxyl groups include known compounds obtained, for example, by polymerization of epoxides, such as ethylene oxide, propylene oxide, butylene oxide, tetrahydrofuran, styrene oxide, or epichlorohydrin. The epoxides can be polymerized on their own, for example in the presence of $BF_3$, or by adding these epoxides, optionally in admixture or successively, onto starter components containing reactive hydrogen atoms, such as water, alcohols, or amines. Suitable starter components include, for example, ethylene glycol, 1,3- or 1,2-propylene glycol, trimethylolpropane, 4,4'-dihydroxydiphenylpropane, aniline, ammonia, ethanolamine, and ethylenediamine. Other suitable polyethers containing hydroxyl groups include sucrose polyethers of the type described, for example, in German Auslegeschrift 1,176,358 and 1,064,938, may also be used in accordance with the invention; polyethers having predominantly primary OH groups (up to 90% by weight, based on all the OH groups present in the polyether); polyethers modified by vinyl polymers, of the type formed for example by polymerization of styrene and acrylonitrile in the presence of polyethers (U.S. Pat. Nos. 3,383,351, 3,304,273, 3,523,093, and 3,110,695; German Patentschrift 1,152,536); and polybutadienes containing OH groups.

Suitable polyacetals include, for example, compounds obtainable from formaldehyde and glycols, such as di- or triethylene glycol, 4,4.-dihydroxyethoxydiphenylmethane, and hexanediol, or even by polymerization of cyclic acetals, such as trioxane.

Suitable polycarbonates containing hydroxyl groups include compounds that may be obtained, for example, by reaction of diols, such as propane-1,3-diol, butane-1,4-diol, hexane-1,6-diol, di-, tri- or tetraethylene glycol, or thiodiglycol, with diarylcarbonates, such as diphenyl carbonate, or phosgene (German Auslegeschriften 1,694,080, 1,915,908, and 2,221,751 and German Offenlegungsschrift 2,605,024).

Suitable polyesters of dicarboxylic acids and diols include those of adipic acid and isophthalic acid and linear and/or branched diols, as well as lactone polyesters, preferably based on caprolactone and starter diols.

Suitable polythioethers include condensation products of thiodiglycol, either on its own or with other glycols.

Other suitable polyhydroxyl compounds for the production of isocyanate prepolymers include polyhydroxyl compounds already containing urethane or urea groups; optionally modified natural polyols; and addition products of alkylene oxides with phenol-formaldehyde resins or even with urea formaldehyde resins may also be used in accordance with the invention. Amide groups may also be introduced into the polyhydroxyl compounds, for example, in accordance with German Offenlegungsschrift 2,559,372.

It is also possible to use polyhydroxyl compounds containing high molecular weight polyadducts or polycondensates or polymers in finely disperse or dissolved form. Polyhydroxyl compounds such as these are obtained, for example, by polyaddition reactions (for example reactions between isocyanates and aminofunctional compounds) or polycondensation reactions (for example between formaldehyde and phenols and/or amines) in situ in the above-mentioned compounds containing hydroxyl groups. Processes such as these are described, for example, in German Auslegeschriften 1,160,075 and 1,260,142 and in German Offenlegungsschriften 2,324,134, 2,423,984, 2,512,385, 2,513,815, 2,550,796, 2,550,797, 2,550,833, 2,550,862, 2,633,293, and 2,639,254. However, it is also possible to mix an aqueous polymer dispersion with a polyhydroxyl compound and then to remove the water from the mixture in accordance with U.S Pat. Nos. 3,869,413 and 2,550,860.

Also suitable are polyhydroxyl compounds modified by vinyl polymers, of the type obtained, for example, by polymerization of styrene and acrylonitrile in the presence of polyethers (U.S. Pat. Nos. 3,383,351, 3,304,273, 3,523,093, and 3,110,695 and German Auslegeschrift 1,152,536) or polycarbonate polyols (German Patentschrift 1,769,795 and U.S. Pat. No. 3,637,909), are also suitable for the process according to the invention. When using polyether polyols modified in accordance with German Offenlegungsschriften 2,442,101, 2,644,922, and 2,646,141 by graft polymerization with vinyl phosphonic acid esters and, optionally, (meth)acrylonitrile, (meth)acrylamide, or hydroxy-functional (meth)acrylates, particularly flame-resistant plastics are obtained.

Other suitable, although less preferred, polyhydroxyl compounds used to prepare prepolymer components (i) include organofunctional polysiloxanes containing two terminal isocyanate-reactive groups and structural units of the formula —O—Si(R)$_2$—, wherein R is C$_1$-C$_4$ alkyl or phenyl (preferably methyl). Suitable starting materials can be either pure polysiloxanes containing terminal organofunctional groups or siloxane-polyoxyalkylene copolymers containing terminal organofunctional groups. Also suitable, although less preferred, are organopolysiloxanes corresponding to the general formula

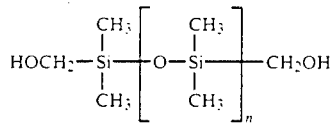

wherein n is an integer form about 5 to about 29. Such compounds are obtained in known manner by equilibration of 1,1,2,3-tetramethyl-1,3-hydroxymethyldisiloxane of the formula

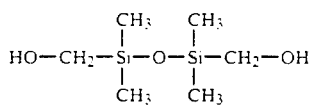

with octamethylcyclotetrasiloxane in the presence of sulfuric acid or by the process according to German Auslegeschrift 1,236,505.

Mixtures of the above-mentioned isocyanates, polyamines, polythiols, and polyhydroxyl compounds may, of course, also be used for the preparation of the starting compounds (i). Such mixtures may be reacted by the standard isocyanate polyaddition process (optionally in the presence of the catalysts and auxiliaries typically used in polyurethane chemistry) in the absence or, preferably, in the presence of organic solvents in which the subsequent urethane alkylation (step (b) of the process) is also carried out.

Particularly preferred isocyanates (i) are isocyanate-terminated prepolymers having a molecular weight in the range from about 400 to about 4000 and based on commercially available diisocyanates having a molecular weight in the range from about 100 to about 400 and alkanediols, polyether diols, or polycarbonate diols.

Suitable starting materials (ii) include oxetane methanols substituted in the 3-position and having the general formula

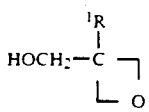

wherein $^1R$ is a hydrocarbon group having a molecular weight of from about 15 to about 200.

Examples of suitable oxetane methanols of this type include 3-tolyl-, 3-phenyl-, 3-benzyl-, 3-hexyl-, 3-pentyl-, 3-butyl-, 3-propyl-, and, preferably, 3-ethyl- and 3-methyl-oxetane methanol.

In carrying out step (a) of the process according to the invention, the quantity of starting material (ii) is generally selected so that one molecule (ii) is available for every NCO group of the starting compound (i). Accordingly, the products resulting from this reaction generally contain no unreacted NCO groups.

The reaction of the starting materials (i) and (ii) according to the invention may be carried out in the absence or, preferably, in the presence of an organic solvent, and optionally in the presence of the catalysts and auxiliaries typically used in polyurethane chemistry. The preferred solvents include those in which the subsequent urethane alkylation (step (b) of the process) may also be performed. Suitable organic solvents include, for example, benzene, toluene, xylene, chlorobenzene, dichlorobenzene, trichlorobenzene, diethyl ether, diisopropyl ether, tert-butyl methyl ether, tetrahydrofuran, dioxane, ethylene glycol dimethyl ether, ethyl acetate, acetone, methyl ethyl ketone, acetonitrile, furfurol, methylene chloride, chloroform, trichloroethylene, tetrachloroethylene, nitromethane, and nitropropane. Preferred solvents include polar aprotic solvents, such as dimethylform-amide, dimethylacetamide, N-methylpyrrolidinone, tetramethyl urea, N-methylcaprolactam, dimethylsulfoxide, tetramethylene-sulfone, hexamethylene phosphoric acid triamide, and the like. Dimethylformamide, dimethylsulfoxide, and N-methylpyrrolidinone are particularly preferred. Mixtures of the above-mentioned solvents may, of course, also be used.

The quantity of solvent used is generally selected so as to be sufficient for clearly dissolving the starting materials (i) and (ii). In practice, this means that the solvents are generally used in a quantity of about 50 to about 1000 parts by weight (preferably about 100 to about 500 parts by weight) for every 100 parts by weight of the mixture of components (i) and (ii).

The reaction is generally carried out at a temperature in the range from about 0° to about 140° C. (preferably at a temperature in the range from about 20° to about 90° C.) under excess pressure, reduced pressure, or preferably in the substantial absence of pressure, and either continuously or discontinuously.

Step (a) of the process according to the invention may be carried out, for example, by initially introducing starting component (i) in the selected solvent (preferably already prepared in that solvent); adding starting component (ii), optionally dissolved in the particular solvent; and then stirring the resulting mixture, optionally at elevated temperature, until isocyanate can no longer be detected in the reaction mixture by infrared spectroscopy.

The product solution from step (a) is test introduced directly into step (b) of the process of the invention.

In step (b) of the process, the intermediate products obtained in step (a) of the process react with alkylating or arylating agents (iii). For the purposes of this invention, alkylating agents include chemical substances that during step (b) of the process of the invention form N-substituted urethanes in which $^2R$ is alkyl, cycloalkyl, or aralkyl. Similarly, for the purposes of this invention, arylating agents include chemical substances that during step (b) of the process form N-substituted urethanes in which $^2R$ is aryl. Suitable alkylating or arylating agents include compounds of the formula $$^2RA$$

wherein
$^2R$ is an aromatic hydrocarbon group containing from 6 to about 18 (preferably from 6 to 13) carbon atoms; an aliphatic hydrocarbon group containing from 1 to about 18 (preferably from 1 to 12) carbon atoms; a cycloaliphatic hydrocarbon group containing from about 7 to about 30 (preferably from 7 to 15) carbon atoms; or an araliphatic hydrocarbon group containing from about 7 to about 39 (preferably 7 to 15) carbon atoms; and
A is a suitable leaving group for alkylation or arylation, such as halide or a sulfate, sulfonate, phosphate, or phosphonate group.

The radical $^2R$ of the alkylating or arylating agent may, of course, be substituted with other functional groups besides the leaving group A. Such other functional groups must, however, be essentially inert under the reaction conditions or react in a defined manner with the other chemical reagents used in the invention. Examples of such other functional groups include nitro groups; certain ester, urethane, amide, and sulfonyl groups; non-activated, aromatically bound halogen; certain epoxide and aziridine groups; ether groups; thioether groups; and other similar groups. Examples of suitable alkylating agents include methyl chloride, methyl bromide, ethyl chloride, ethyl bromide, propyl chloride, propyl bromide, i-propyl chloride, i-propyl bromide, butyl chloride, butyl bromide, isobutyl chloride, isobutyl bromide, cyclohexyl chloride, cyclohexyl bromide, octyl, nonyl, decyl, undecyl and dodecyl chloride and bromide, benzyl chloride, benzyl bromide, allyl chloride, allyl bromide, p-nitrobenzyl chloride, p-nitrobenzyl bromide, dimethyl sulfate, diethyl sulfate, p-toluenesulfonic acid methyl ester, p-toluenesulfonic acid ethyl ester, ethylene chlorohydrin, ethylene bromohydrin, and epichlorohydrin. Examples of suitable arylating agents include 2,4-dinitrochlorobenzene, 2,4-dinitrofluorobenzene, 2,4-trinitrochlorobenzene, and 2,4,6-trinitroflourobenzene. Particularly preferred alkylating agents are benzyl chloride, benzyl bromide, as well as methyl chloride and methyl bromide. Mixtures of these alkylating and arylating agents may of course also be used.

When group Z contains functional groups that can react with alkylating or arylating agents, group Z can be converted to a different group, represented by Y. Thus, groups Y and Z may be identical but are not necessarily identical. In the preferred embodiments, in which Y is an n-functional (preferably difunctional) hydrocarbon group, Y is typically the same as Z. Surprisingly, this alkylation step according to the invention is not accompanied by significant cleavage of the urethane ester bond, which would presumably involve attack on the carbonyl oxygen atom and concomitant elimination. The alkylation step is also not accompanied by significant ring-opening of the oxetane group, which would give rise to undesirable alkylated ring-opened compounds unlike those formed in step (c) of the invention.

Step (b) of the process of the invention is carried out in the presence of metal hydroxides, for example alkali metal hydroxides such as potassium or sodium hydroxide. Sodium hydroxide is preferred for economic reasons. It is, of course, also possible to use lithium, rubidium, and barium hydroxides or even moist silver oxide. Using mixtures of these metal hydroxides may also be advantageous.

It can be advantageous to carry out the reaction of step (b) in the presence of a phase-transfer catalyst. Phase-transfer catalysts are described, for example, in E.V. and S.S. Dehmlow, Phase Transfer Catalysis, 2nd Edition, Verlag Chemie (1983). Suitable catalysts include quaternary ammonium or phosphonium salts of the formula

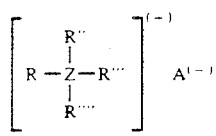

wherein
Z is nitrogen or phosphorus;
R' is $C_1$-$C_{18}$ alkyl or a $C_7$-$C_{15}$ araliphatic group;
R'', R''', and R'''' are independently $C_1$-$C_{18}$ alkyl (with the sum of the number of carbon atoms in R',R'', R''', and R'''' preferably being between about 12 and about 31); and
$A^{(-)}$ is a suitable counterion, preferably being the same as the leaving group of the alklating or arylating agent, such as halide or a sulfate, sulfonate, phosphate, or phosphonate group.

Examples of suitable phase-transfer catalysts include N-benzyl-N,N,N-trimethylammonium and N-benzyl-N,N,N-triethylammonium chloride or bromide, N-benzyl-N-dodecyl N,N-dimethylammonium chloride or bromide, N,N,N,N-tetrahexylammonium chloride or bromide, N-benzyl-N,N,N-trioctylammonium chloride or bromide, or the phosphonium salts corresponding to these ammonium salts. In the practical application of the process according to the invention, the quaternary ammonium or phosphonium salts mentioned by way of example are preferably used as such or in the form of aqueous solutions (for example, having solids contents of about 30 to about 60% by weight) and preferably in a quantity of about 1 to about 10 mol-% based on the molar number of the urethane groups present.

Where polar aprotic solvents, such as dimethylformamide, dimethylacetamide, N-methylpyrrolidone, or dimethylsulfoxide (the preferred solvents), are used in step (b), the alkylation or arylation may be carried out in the absence of phase transfer catalysts with no disadvantages.

In step (b) of the process according to the invention, the alkylating or arylating agents (iii) may be used in stoichiometric quantities, as well as in super- or substoichiometric quantities, based on the urethane groups present in the intermediate products of step (a) of the process. In determining stoichiometry, any urethane groups already present in the starting component (i) should be taken into account. When a substoichiometric quantity of alkylating or arylating agent is used, only partial alkylation or arylation is, of course, achieved, whereas using a relatively large excess is uneconomical. The amount of component (iii) is preferably selected in such a way that about 1 to about 1.5 mole of component (iii) is present for every mole of urethane groups in the intermediate products of step (a). The hydrogen halide or other acidic materials released during the reaction may be bound by addition of metal hydroxides. The quantity metal hydroxides used is selected so that it is at least sufficient to neutralize the hydrogen halide or other acid released. The metal hydroxides are preferably used in such a o quantity that about 1 to about 3 mole of base equivalents are available per mole of urethane groups.

As already mentioned, step (b) of the process of the invention is carried out in a suitable organic solvent. Suitable solvents include, for example, the solvents mentioned in the description of step (a) of the process and can be used in the same quantities.

Step (b) of the process of the invention is generally carried out at about 10° to about (preferably at 20° to 60° C.) under excess pressure, reduced pressure, or preferably in the substantial absence of pressure, and either continuously or discontinuously. Where readily volatile alkylating agents, such as, for example, methyl chloride, methyl bromide or ethyl chloride, are used, it is best to carry out the reaction under pressure in an autoclave. When under pressure, the reaction may be carried out either in an aprotic organic solvent or in excess liquefied alkylating agent as solvent, and optionally in the presence of a phase transfer catalyst. The residence time for the alkylation or arylation reaction is generally from 0.5 to 24 hours (preferably from 0.5 to 8 hours).

Step (b) of the process may be carried out, for example, by initially introducing the starting materials (optionally together with phase-transfer catalyst) in the selected solvent and then continuously adding the base in dissolved or suspended form (preferably in finely ground solid form), either in portions or continuously, with stirring and optionally with cooling. The reaction mixture is then stirred at room temperature or, optionally, at elevated temperature until infrared spectroscopy indicates complete conversion of the urethane groups initially present or until starting material (iii) can no longer be detected by thin-layer or gas chromatography.

The reaction mixture is worked up in known manner. The reaction mixture is preferably diluted with a substantially inert water-immiscible solvent and washed with water or salt solution until neutral. The solvents, if any, are distilled off in vacuo and the reaction product is dried in vacuo. The reaction mixture may also be neutralized by treatment with carbon dioxide. Examples of suitable inert solvents include toluene, methylene chloride, chlorobenzene, dichlorobenzene, 1,2-dichloroethane, trichloroethylene, and other such inert solvents known in the art. The crude product thus obtained may generally be subsequently processed without further purification. However, if small quantities of starting material (ii) should still be present due to an incomplete reaction, they may be conveniently removed by thin-layer distillation. It is also possible in principle, although less preferred, to introduce the reaction mixture obtained in step (b), optionally after neutralization of excess alkali hydroxide, directly into step (c) (i.e., without intermediate isolation).

The completely or partly alkylated or arylated oxetane-containing compounds obtained in step (b) of the process according to the invention are reacted with strong acids in step (c) of the process to form hydroxyl-terminated compounds. During step (c) of the process, the residue of the strong acid that remains after dissociation (i.e., the anionic portion) may be incorporated into the ring-opened product as substituent X, although, depending on specific reaction conditions, X may be a hydroxyl group instead. During the acid treatment of step (c), the moiety Y that is present in the product of step (b) may be transformed, depending on the sensitivity of Y to acid according to principles readily understood by one skilled in the art, into a different moiety. In the preferred embodiments, in which Y is an n-functional (preferably difunctional) hydrocarbon group, Y is typically unchanged by acids. Moiety Y is preferably phenylene or a $C_1$-$C_6$ alkylated phenylene (more preferably 2,4- or 2,6-tolylene or a mixture thereof), derived from the corresponding diisocyanatobenzene; 4,4'-methylenediphenylene, derived from the corresponding 4,4'-diisocyanatodiphenylmethane; or an alkylene (preferably 1,6-hexamethylene), derived from the corresponding alkylene diisocyanate.

Suitable acids for use in step (c) of the process include strong monobasic or polybasic organic and inorganic acids. Examples of suitable acids include trifluoroacetic and trichloroacetic acid; methanesulfonic, chloromethanesulfonic, ethanesulfonic, 2-chloroethanesulfonic, propanesulfonic, butanesulfonic, perfluorobutanesulfonic, 4-chlorobutanesulfonic, perfluoroethanesulfonic, 2-hydroxyethanesulfonic, benzene-sulfonic, 2-, 3-, and 4-chlorobenzenesulfonic, 2,5- and 3,4-dichlorobenzenesulfonic, 2-, 3-, and 4-nitrobenzenesulfonic, 4-chloro-3-nitrobenzenesulfonic, 2-chloro-5-nitrobenzene-sulfonic, 2,4-nitrobenzenesulfonic, 4-methylbenzenesulfonic, 1-naphthalenesulfonic, 5-nitro-1-naphthalenesulfonic, 1,3-benzenedisulfonic, 5-nitro-1,3-benzenedisulfonic, 1,5-,1,6-, 2,6-, and 2,7-naphthalenedisulfonic, 1,1'-biphenyl-4,4'-disulfonic, and 2-, 3-, and 4-hydroxybenzenesulfonic acids; and inorganic acids, such as, for example, nitric, phosphoric, sulfuric, perchloric, chloric, perbromic, bromic, periodic, iodic, and hydrofluoric acids and, preferably, hydrochloric acid, hydrobromic acid, and hydriodic acid.

In step (c) of the process according to the invention, the acid may be used in stoichiometric quantities, as well as in super- or substoichiometric quantities, based on the oxetane groups present in the intermediate products of step (b) of the process. When a substoichiometric quantity of acid is used, not all of the oxetane groups present can react with ring opening and formation of hydroxyl groups, whereas using a relatively large excess of acid is uneconomical. The quantity of acid used is preferably selected in such a way that about 1 to about 2 mole of acid are present for every mole of oxetane groups in the intermediate products of step (b).

Step (c) of the process of the invention is preferably carried out in an organic solvent. Suitable solvents include, for example, the solvents already mentioned in the description of steps (a) and (b) of the process and can be used in the same quantities. Preferred solvents include diisopropyl ether, ethylene glycol dimethyl ether, diethyl ether, tetrahydrofuran, and dioxane. Step (c) is generally carried out at 10° to (preferably at 20° to 60° C.) under excess pressure, reduced pressure, or preferably in the absence of pressure, and either continuously or discontinuously. The residence time is generally from 0.5 to 24 hours (preferably from 0.5 to 8 hours).

Step (c) of the process of the invention may be carried out, for example, by initially introducing the intermediate products of step (b) in the selected solvent and then adding the acid in solid form, gaseous form, or preferably, dissolved form, either continuously or in portions, and optionally with cooling. The reaction mixture is then stirred at room temperature or, optionally, at elevated temperature until reaction is complete, as indicated, for example, by the titrimetric consumption of acid. The reaction mixture is worked up in known manner, preferably by the method described in reference to step (b) of the process.

The hydroxyl-terminated N,N-disubstituted oligo- or polyurethanes obtainable by the process according to the invention are valuable starting materials for the production of thermostable plastics. In particular, the hydroxyl-terminated N,N-disubstituted urethanes according to the invention exhibit greater thermal, thermo-oxidative, and photooxidative stability (see R. Vieweg, A. Hochtlen, *Kunststoff Handbuch*, Vol. VII, Polyurethane, Hanser Verlag, Munich 1966, pages 11 and 21) and more favorable fire behavior than the corresponding N-monosubstituted urethanes. Compounds according to this invention are suitable as reactants, such as chain extenders and crosslinking agents, for optionally blocked polyisocyanates in the production of polyurethanes (polyurethane ureas), optionally cellular polyurethane plastics or polyurethane foams, for which purpose they may also be combined with other low molecular weight compounds (molecular weight 32 to 399) and/or relatively high molecular weight compounds (molecular weight 400 to about 12,000) containing isocyanate-reactive groups. Suitable starting components for the production of polyurethane plastics are mentioned, for example, in German Offenlegungsschriften 2,302,564, 2,432,764 (believed to correspond to U.S. Pat. No. 3 903,679), 2,639,083, 2,512,385, 2,513,815, 2,550,796, 2,550,797, 2,550,833, 2,550,860, and 2,550,862, where references to auxiliaries and additives optionally used in the production of polyurethanes can also be found.

The present invention also relates to the production of polyurethane plastics using the polyhydroxyl compounds according to the invention. For elastomers, coatings, and filaments, for example, compounds of this invention may be applied from melts, solutions, or dispersions or as mixtures of reactive components. Other applications known for relatively high molecular weight polyhydroxyl compounds may, of course, also be considered.

The following examples further illustrate details for the preparation of the compounds of this invention. The invention, which is set forth in the foregoing disclosure, is not to be limited either in spirit or scope by these examples. Those skilled in the art will readily understand that known variations of the conditions and processes of the following preparative procedures can be used. Unless otherwise noted, all temperatures are degrees Celsius and all percentages are percentages by weight. The mean particle size of the powder-form alkali hydroxide used is from 6 to 9 μm.

DESCRIPTION OF THE PREFERRED EMBODIMENTS

Example 1 a) Preparation of the oxetane-terminated starting urethane

A 2,4-diisocyanatoalkylbenzene mixture of homologs and isomers of isocyanates having alkyl radicals with 8 to 15 carbon atoms prepared according to EP 58,368 (194.4 g, 0.6 mole) is added dropwise with stirring over a period of 2 hours at room temperature to a solution of hexane-1,6-diol (59 g, 0.5 mole) in 645.4 g freshly distilled dimethylformamide (DMF), followed by stirring for 80 minutes at 80° C. 3-Ethyl-3-oxetane methanol (23.2 g, 0.2 mol) is then added, followed by stirring at 80° C. until isocyanate can no longer be detected by infrared (IR) spectroscopy. The desired material is obtained as a clear yellowish solution having a solids content of approximately 30%.

Flow viscosity: 14 s (4 mm Ford cup, 25° C.).

b) Urethane alkylation

Methyl chloride (27.8 g, 0.55 mole) is rapidly added under pressure in an autoclave to a dispersion of powdered sodium hydroxide (26.4 g, 0.66 mole) in a 30% solution of urethane according to Example 1a) (333 g, 0.43 mole urethane). The mixture is stirred first for 3 hours at room temperature and then for 3 hours at 60° C. The cooled and vented reaction mixture is diluted with approximately 1 liter chlorobenzene, filtered, and washed with water until neutral. After drying over sodium sulfate, the solvent is distilled off in vacuo. Yield: 105 g (quantitative) of a clear brownish viscous oil. IR: missing bands at 3200-3500 cm$^{-1}$ indicate complete substitution of the urethane protons.

c) Ring-opening reaction of the terminal oxetane groups with acid

Hydrobromic acid (48%; 37.3 g) is added dropwise with stirring over a period of 20 minutes at room temperature to a solution of 200 g methylated urethane according to Example 1b) in 450 ml dioxane, followed by stirring for 4 hours at 60° C. The cooled reaction mixture is diluted with about 900 ml methylene chloride and washed with water until neutral. After drying over sodium sulfate, the solvent is distilled off in vacuo. Yield: 200 g of a yellow-brown oil.

Viscosity: 4600 mPa.s/85° C.
OH value: 30

Example 2 a) Oxetane-terminated starting urethane Prepared as in Example 1a).

b) Urethane alkylation

Powdered sodium hydroxide (52 g, 1.3 mole) is added in uniform portions with stirring over a period of 1 hour at room temperature to a solution of a 30% urethane solution according to Example 1a) (766 g, 1 mole urethane) and 151.9 g (1.2 mole) benzyl chloride. The mixture is stirred for 3 hours at room temperature and then for 3 hours at 50° C. After cooling, the reaction product is worked up as in Example 1b). Yield: 298 g (93% theory) of a clear brown viscous oil. IR: missing bands at 3200-3500 cm$^{-1}$ indicate complete substitution of the urethane protons.

c) Oxetane opening

Benzylated urethane according to Example 2b) (269.4 g) and hydrobromic acid (48%; 40.2 g) are reacted in 550 ml dioxane as in Example 1c). Yield: 243 g of a clear brown resin.

Viscosity: 7000 mPa.s/85° C.
OH value: 28

Example 3 a) Oxetane-terminated starting urethane

Hexane-1,6-diol (70.8 g, 0.6 mole), 4,4'-diisocyanatodiphenylmethane (187.5 g, 0.75 mole), and 3-ethyl-3-oxetane methanol (34.8 g, 0.3 mole) are reacted in 684 g freshly distilled DMF as in Example 1a). The desired material is obtained as a clear light brown solution having a solids content of 30%.

Flow viscosity: 31 s (4 mm Ford cup, 25° C.).

b) Urethane alkylation

A 30% urethane solution according to Example 3a) (1000 g, 1.54 mole urethane), powdered sodium hydroxide (80 g, mole), and methyl chloride (101 g, 2 mole) are reacted as in Example 1b). Yield: 296 g (92% theory) of a clear brownish viscous oil.

IR: missing bands at 3200-3500 cm$^{-1}$ indicate complete substitution of the urethane protons.

c) Oxetane opening

Methylated urethane according to Example 3b) (261.8 g) and hydrobromic acid (48%; 71.1 g) are reacted in 550 ml tetrahydrofuran as in Example 1c). Yield: 234 g of a clear brown resin.

Viscosity: 10,400 mPa s/25° C.
OH value: 40.

Example 4 a) Oxetane-terminated starting urethane Prepared as in Example 3a).

b) Urethane alkylation

A 30% urethane solution according to Example 3a) (651 g, 1 mole urethane), benzyl chloride (151.9 g, 1.2 mole), and powdered sodium hydroxide (52 g, 1.3 mole) are reacted as in Example 2b). Yield: 271 g (95% theory) of a clear light brown viscous oil.

IR: very weak bands at 3200-3500 cm$^{-1}$ indicate almost complete substitution of the urethane protons.

c) Oxetane opening

Benzylated urethane according to Example 4b) (243 g) and hydrobromic acid (48%; 48.8 g) are reacted in 500 ml dioxane as in Example 1c). Yield: 191 g of a clear brown resin.

Viscosity: 83,630 mPa.s/85° C.
OH value: 34.

Example 5 a) Oxetane-terminated starting urethane

Hexane-1,6-diol (236 g, 2 mole), tolylene diisocyanate (2,4-isomer content: 80%) (435 g, 2.5 mole), and 3-ethyl-3-oxetane methanol (116 g, 1 mole) are reacted in 1836 g freshly distilled DMF as in Example 1a). The desired material is obtained as a clear yellowish solution having a solids content of 30%.

Flow viscosity: 17 s (4 mm Ford cup, 25° C.).

b) Urethane alkylation

A 30% urethane solution according to Example 5a) (1050 g, 2 mole urethane), powdered sodium hydroxide (108 g, 2.7 mole), and methyl chloride (121.2 g, 2.4 mole) are reacted as in Example 1b). Yield: 296 g (86% theory) of a clear brownish viscous oil.

IR missing bands at 3200–3500 cm$^{-1}$ indicate complete substitution of the urethane protons.

c) Oxetane opening

Methylated urethane according to Example 5b) (250 g) and hydrobromic acid (48%; 77 g) are reacted in 500 ml dioxane as in Example 1c). Yield: 202 g of a clear brown resin.
Viscosity: 8800 mPa.s/85° C.
OH value: 59

Example 6 a) Oxetane-terminated starting urethane

Hexane-1,6-diol (141.6 g, 1.2 mole), tolylene diisocyanate (2,4-isomer content: 80%) (243.6 g, 1.4 mole), and 3-ethyl-3-oxetane methanol (46.4 g, 0.4 mole) are reacted in 1294.8 g freshly distilled DMF as in Example 1a). The desired material is obtained as a clear yellowish solution having a solids content of 25%.
Flow viscosity: 15 s (4 mm Ford cup, 25° C.).

b) Urethane alkylation

A 25% urethane solution according to Example 6a) (616 g, 1 mole urethane), benzyl chloride (151.9 g, 1.2 mole), and powdered sodium hydroxide (52 g, 1.3 mole) are reacted as in Example 2b). Yield: 244 g (quantitative) of a clear red-brown viscous oil.

IR: very weak bands at 3200–3500 cm$^{-1}$ indicate almost complete substitution of the urethane protons.

c) Oxetane opening

Benzylated urethane according to Example 6b) (205 g) and hydrobromic acid (48%; 34.4 g) are reacted in 450 ml dioxane as in Example 1c). Yield: 180 g of a clear brown resin.
Viscosity: 67,780 mPa.s/85° C.
OH value: 30.

Example 7 a) Oxetane-terminated starting urethane

3-Methylpentane-1,5-diol (141.6 g, 1.2 mole), hexamethylene diisocyanate (235.2 g, 1.4 mole), and 3-ethyl-3-oxetane methanol (46.4 g, 0.4 mole) are reacted in 987.4 g freshly distilled DMF as in Example 1a). The desired material is obtained as a clear yellowish solution having a solids content of 30% which solidifies into an ointment-like mass on prolonged standing.
Flow viscosity: 17 s (4 mm Ford cup, 25° C.).

b) Urethane alkylation

A molten 30% urethane solution according to Example 7a) (350 g, 0.7 mole urethane), methyl bromide (80 g, 0.84 mole), and powdered sodium hydroxide (32 g, 0.8 mole) are reacted as in Example 2b). Yield: 53 g of a yellowish viscous oil.

IR: a weak band at 3300 cm$^{-1}$ indicates an incomplete reaction.

c) Oxetane opening

Methylated urethane according to Example 7b) (110 g) and hydrobromic acid (48%; 28.7 g) are reacted in 300 ml dioxane as in Example 1c). Yield: 97 g of a clear yellowish resin.
Viscosity: 17,820 mPa.s/85° C.
OH value: 43.

Example 8 a) Oxetane-terminated starting urethane

A diisocyanatotoluene mixture (80% 2,4-, 20% 2,6-) (522 g, 3 mole) is added dropwise with stirring over a period of 3 hours at room temperature to a solution of triglycol (300 g, 2 mole) in 2450 g freshly distilled DMF, followed by stirring for 30 minutes at room temperature. 3-Ethyl-3-oxetane methanol (232 g) is then added, followed by stirring at 35° C. until isocyanate can no longer be detected by IR spectroscopy. The desired material is obtained as a clear, yellow-brown solution having a solids content of approximately 30%.
Flow viscosity: 14 s (4 mm Ford cup, 25° C.).

b) Urethane alkylation

Methyl chloride (165 g, 3.3 mole) is rapidly added under pressure in an autoclave to a dispersion of powdered sodium hydroxide (131 g (3.3 mole) in a 30% urethane solution according to Example 8a) (1600 g, 2.7 mole urethane). The mixture is stirred for 3 hours at room temperature and then for 2 hours at 50° C. The cooled and vented reaction mixture is diluted with approximately 700 ml methylene chloride, filtered, and washed with water until neutral. After drying over sodium sulfate, the solvent is distilled off in vacuo. Yield: 445 g (86% theory) of a clear brownish product.
Viscosity: 73,722 mPa.s/50° C.

IR: relatively weak bands at 3200–3500 cm$^{-1}$ indicate almost complete substitution of the urethane protons.

c) Oxetane opening

Hydrobromic acid (48%; 155 g, 0.9 mole) is added dropwise over a period of 1 hour with stirring at room temperature to a solution of methylated urethane according to Example 8b) (350 g, 0.6 mole) in 525 ml dioxane. The mixture is stirred for 1 hour at room temperature and for 3 hours at 50° C. The cooled reaction mixture is diluted with approximately 800 ml methylene chloride, filtered, and washed with water until neutral. After drying over sodium sulfate, the solvent is distilled off in vacuo. Yield: 370 g (95% theory) of a clear brown viscous substance.
Viscosity: 116,370 mPa.s/ 50°.
OH value: 97.

Example 9 a) Oxetane-terminated starting urethane

Dipropylene glycol (268 g, 2 mole), a diisocyanatotoluene mixture (80% 2,4-, 20% 2,6-) (522 g, 3 mole) and 3-ethyl-3-oxetane methanol (232 g, 2 mole) are reacted in 2385 g freshly distilled DMF as in Example 8a). The desired material is obtained as a clear yellow-brown substance.
Flow viscosity: 145 s (4 Ford cup, 25° C.).

b) Urethane alkylation

A 30% urethane solution according to Example 9a) (1600 g, 2.8 mole urethane), powdered sodium hydroxide (136 g, 3.4 mole), and methyl chloride (171 g, 2.4 mole) are reacted as in Example 8b). Yield: 476 g (92% theory) of a light brown substance.

IR: relatively weak bands at 3200-3500 cm$^{-1}$ indicate almost complete substitution of the urethane protons.

c) Oxetane opening

Methylated urethane according to Example 9b) (200 g, 0.36 mole) and hydrochloric acid (37%; 53.3 g, 0.54 mole) are reacted in 300 ml dioxane as in Example 8c). Yield: 160 g (70% theory) of a clear light brown substance.

Viscosity: cannot be measured (too hard).
OH value: 99.

Example 10 a) Oxetane-terminated starting urethane

Dipropylene glycol (402 g, 3 mole), a diisocyanatotoluene mixture (80% 2,4-, 20% 2,6-) (696 g, 4 mole), and 3-ethyl-3-oxetane methanol (232 g, 2 mole) are reacted in 3103 g freshly distilled DMF as in Example 8a). The desired material is obtained as a clear yellow-brown substance.

Flow viscosity: 14 s (4 mm Ford cup, 25° C.).

b) Urethane alkylation

A 30% urethane solution according to Example 10a) (1400 g, 2.5 mole urethane), powdered sodium hydroxide (121 g, 3.0 mole), and methyl chloride (153 g, 3.0 mole) are reacted as in Example 8b). Yield: 373 g (82% theory) of a dark brown substance.

Viscosity: 7221 mPa.s/80° C.
IR: relatively weak bands at 3200-3500 cm$^{-1}$ indicate almost complete substitution of the urethane protons.

c) Oxetane opening

Methylated urethane according to Example 10b) (300 g, 0.42 mole) and hydrobromic acid (48%; 104.6 g, 0.62 mole) are reacted in 450 ml dioxane as in Example 8c). Yield: 282 g (84% theory) of a clear light brown substance.

Viscosity: 2590 mPa.s/50° C.
OH value: 84.

Example 11 a) Oxetane-terminated starting urethane

A two-thirds portion of a diisocyanatotoluene mixture (80% 2,4-, 20% 2,6-) (522 g, 3 mole) is added dropwise with stirring over a period of 2 hours at room temperature to a solution of polyglycol 400 (800 g, 2 mole) in 262 g freshly distilled DMF. 3-Ethyl-3-oxetane methanol (232 g, 2 mole) is then added, followed by stirring for 10 minutes at room temperature. The remaining portion of the diisocyanatotoluene mixture is then added dropwise over a period of 1 hour, followed by stirring at room temperature until isocyanate can no longer be detected by IR spectroscopy. The desired material is obtained as a clear yellow-brown substance.

Flow viscosity: 24 s (4 mm Ford cup, 25° C.).

b) Urethane alkylation

A 30% urethane solution according to Example 11a) (1600 g, 1.8 mole urethane), powdered sodium hydroxide (80 g, 2.0 mole), and methyl chloride (112 g, 2.2 mole) are reacted as in Example 8b). Yield: 445 g (88% theory) of a clear yellow brown substance.

Viscosity: 4562 mPa.s/50° C.
IR: relatively weak bands at 3200-3500 cm$^{-1}$ indicate almost complete substitution of the urethane protons.

c) Oxetane opening

Methylated urethane according to Example 11b) (380 g, 0.46 mole) and hydrobromic acid (48%; 116 g, 0.69 mole) are reacted in 500 ml dioxane as in Example 8c). Yield: 348 g (84% theory) of a clear light yellow substance.

Viscosity: 10649 mPa.s/50° C.
OH value: 75.

What is claimed is:

1. A compound having the formula

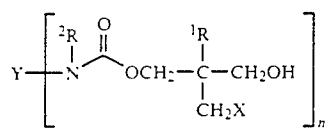

wherein

X is the residue of a strong monobasic or polybasic acid remaining after dissociation of the proton or protons of said acid or a hydroxyl group;

Y is an n-functional hydrocarbon group having a molecular weight of from about 15 to about 8000 and optionally interrupted by oxygen, sulfur, or silicon atoms, or by ester, carbonate, urea, N-monosubstituted urethane, or N,N-disubstituted urethane groups;

$^1$R is hydrogen or a hydrocarbon group having a molecular weight of from about 15 to about 200;

$^2$R is the radical of an alkylating or arylating agent; and n is an integer of from 2 to 6.

2. A compound according to claim 1 wherein X is the residue of a strong monobasic acid or a hydroxyl group.

3. A compound according to claim 1 wherein X is a chlorine, bromine, or iodine atom.

4. A compound according to claim 1 wherein Y is a n-functional hydrocarbon group having a molecular weight of from about 15 to about 8000.

5. A compound according to claim 1 wherein Y is a n-functional hydrocarbon group having a molecular weight of from about 15 to about 8000 interrupted by oxygen, sulfur, or silicon atoms, or by ester, carbonate, urea, N-monosubstituted urethane, or N,N-disubstituted urethane groups.

6. A compound according to claim 1 wherein n is an integer of from 2 to 4.

7. A compound according to claim 1 wherein n is 2.

8. A compound according to claim 1 wherein Y is a difunctional hydrocarbon group having a molecular weight of from about 15 to about 8000.

9. A compound according to claim 4 wherein the difunctional hydrocarbon group is selected from the group consisting of 2,4-tolylene, 2,6-tolylene, 4,4'-methylenediphenylene, and 1,6-hexamethylene.

10. A compound according to claim 1 wherein $^1$R is methyl or ethyl.

11. A compound according to claim 1 wherein $^1$R is ethyl.

12. A compound according to claim 1 wherein $^2$R is an aromatic hydrocarbon group containing from 6 to about 18 carbon atoms; an aliphatic hydrocarbon group containing from 1 to about 18 carbon atoms; a cycloaliphatic hydrocarbon group containing from about 7 to about 30 carbon atoms; or an araliphatic hydrocarbon group containing from about 7 to about 39 carbon atoms.

13. A compound according to claim 1 wherein $^2R$ is an aliphatic hydrocarbon group containing from 1 to 12 carbon atoms or an araliphatic hydrocarbon group containing from 7 to 15 carbon atoms.

14. A compound according to claim 1 wherein $^2R$ is methyl or benzyl.

15. A compound according to claim 1 having the formula $$Y \left[ \begin{array}{c} ^2R \quad O \quad\quad ^1R \\ | \quad\quad \| \quad\quad | \\ N{-}C{-}OCH_2{-}C{-}CH_2OH \\ | \\ CH_2X \end{array} \right]_2$$

wherein
X is a chlorine, bromine, or iodine atom;
Y is a difunctional hydrocarbon group having a molecular weight of from about 15 to about 8000;
$^1R$ is methyl or ethyl; and
$^2R$ is methyl or benzyl.

16. A process for the production of an N,N-disubstituted compound containing urethane groups and terminal hydroxyl groups comprising
(a) reacting (i) an n-functional isocyanate-terminated compound of the formula $$Z(NCO)_n$$

with (ii) an oxetane methanol of the formula $$\begin{array}{c} ^1R \\ | \\ HOCH_2{-}C{-}\neg \\ \quad\quad\quad\quad | \\ \quad\quad\quad\quad \llcorner O \end{array}$$

to form an oxetane-terminated compound of the formula $$Z \left[ \begin{array}{c} H \quad O \quad\quad ^1R \\ | \quad\; \| \quad\quad | \\ N{-}C{-}OCH_2{-}C{-}\neg \\ \quad\quad\quad\quad\quad\quad\quad | \\ \quad\quad\quad\quad\quad\quad\quad \llcorner O \end{array} \right]_n ;$$

(b) reacting the oxetane-terminated compound obtained in (a) with (iii) an alkylating or arylating agent in the presence of a metal hydroxide to form a compound of the formula $$Y \left[ \begin{array}{c} ^2R \quad O \quad\quad ^1R \\ | \quad\quad \| \quad\quad | \\ N{-}C{-}OCH_2{-}C{-}\neg \\ \quad\quad\quad\quad\quad\quad\quad | \\ \quad\quad\quad\quad\quad\quad\quad \llcorner O \end{array} \right]_n ; and$$

(c) reacting the compound obtained in (b) with a strong acid to form a hydroxyl-terminated compound of the formula $$Y \left[ \begin{array}{c} ^2R \quad O \quad\quad ^1R \\ | \quad\quad \| \quad\quad | \\ N{-}C{-}OCH_2{-}C{-}CH_2OH \\ | \\ CH_2X \end{array} \right]_n$$

wherein
X is the residue of a strong monobasic or polybasic acid remaining after dissociation of the proton or protons of said acid or a hydroxyl group;
Y is an n-functional hydrocarbon group having a molecular weight of from about 15 to about 8000 and optionally interrupted by oxygen, sulfur, or silicon atoms, or by ester, carbonate, urea, N-monosubstituted urethane, or N,N-disubstituted urethane groups;
Z is an n-functional hydrocarbon group having a molecular weight of from about 15 to about 8000 and optionally interrupted by oxygen, sulfur, or silicon atoms, or by ester, carbonate, urea, or N-monosubstituted urethane groups;
$^1R$ is hydrogen or a hydrocarbon group having a molecular weight of from about 15 to about 200;
$^2R$ is the radical of an alkylating or arylating agent; and
n is an integer of from 1 to 6.

17. A process according to claim 16 wherein step (b) of the process is carried out in an organic solvent in the presence of sodium or potassium hydroxide and a phase transfer catalyst.

18. A process according to claim 17 wherein the organic solvent is selected from the group consisting of dimethylformamide, dimethylacetamide, dimethylsulfoxide, and N-methylpyrrolidinone.

19. A process according to claim 16 wherein the strong acid is selected from the group hydrochloric acid, hydrobromic acid, and hydriodic acid.

20. A process according to claim 16 wherein X is a chlorine, bromine, or iodine atom.

21. A process according to claim 16 wherein Z is a n-functional hydrocarbon group having a molecular weight of from about 15 to about 8000.

22. A process according to claim 16 wherein n is 2 such that the n-functional isocyanate-terminated compound (i) is difunctional.

23. A process according to claim 22 wherein the difunctional isocyanate-terminated compound (i) is selected from the group consisting of 2,4-tolylene diisocyanate, 2,6-tolylene diisocyanate, diphenylmethane-4,4'-diisocyanate, and 1,6-hexamethylene diisocyanate.

24. A process according to claim 16 wherein $^1R$ is methyl or ethyl.

25. A process according to claim 16 wherein $^2R$ is an aromatic hydrocarbon group containing from 6 to about 18 carbon atoms; an aliphatic hydrocarbon group containing from 1 to about 18 carbon atoms; a cycloaliphatic hydrocarbon group containing from about 7 to about 30 carbon atoms; or an araliphatic hydrocarbon group containing from about 7 to about 39 carbon atoms.

26. A compound according to claim 16 wherein $^2R$ is an aliphatic hydrocarbon group containing from 1 to 12 carbon atoms or an araliphatic hydrocarbon group containing from 7 to carbon atoms.

27. A process according to claim 16 wherein $^2R$ is methyl or benzyl.

28. A process according to claim 16 wherein the alkylating agent is selected from the group consisting of methyl chloride, methyl bromide, benzyl chloride, and benzyl bromide.

29. A process according to claim 16 for the production of an N,N-disubstituted compound containing urethane groups and terminal hydroxyl groups comprising
(a) reacting (i) a difunctional isocyanate-terminated compound of the formula

with (ii) an oxetane methanol of the formula

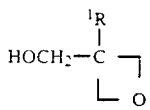

to form an oxetane-terminated compound of the formula

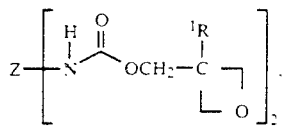

(b) reacting the oxetane-terminated compound obtained in (a) with (iii) methyl chloride, methyl bromide, benzyl chloride, and benzyl bromide in an organic solvent selected from the group consisting of dimethylformamide, dimethylacetamide, dimethylsulfoxide, and N-methylpyrrolidinone in the presence of sodium or potassium hydroxide and a phase transfer catalyst to form a compound of the formula

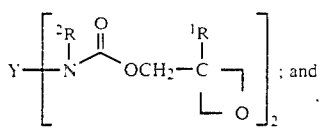 ; and (c) reacting the compound obtained in (b) with hydrochloric acid, hydrobromic acid, or hydriodic acid to form a hydroxyl-terminated compound of the formula

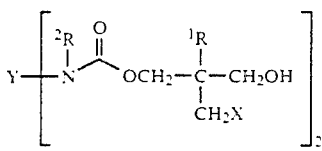

wherein
X is a chlorine, bromine, or iodine atom;
Y is a difunctional hydrocarbon group having a molecular weight of from about 15 to about 8000;
Z is a difunctional hydrocarbon group having a molecular weight of from about .15 to about 8000;
$^1R$ is methyl or ethyl; and
$^2R$ is methyl or benzyl.

* * * * *

UNITED STATES PATENT AND TRADEMARK OFFICE
CERTIFICATE OF CORRECTION

PATENT NO. : 5,099,058

DATED : March 24, 1992

INVENTOR(S) : Josef Sanders and Dieter Dieterich

It is certified that error appears in the above-identified patent and that said Letters Patent is hereby corrected as shown below:

Title page:

--Assignee: Bayer Aktiengesellschaft, Leverkusen Bayerwerk, Fed. Rep. of Germany--.

On the title page, insert:

--Attorney, Agent or Firm: Joseph C. Gil, Godfried R. Akorli--.

On the title page, in the Abstract, at line 2, after the formula, delete "memobasic" and insert --monobasic--.

On the title page, in the Abstract, at line 14, after the formula, insert --n-- before "is an integer of from 2 to about 6".

At column 3, in the first two lines after the 4th formula, delete "r is from 1 to about 6" and insert --n is from 1 to about 6--.

At column 4, line 31, delete "isocyznates" and insert --isocyanates--.

At column 5, lines 24 and 25, delete "bis(3-aminopropyl)meihylamine" and insert --bis(3-aminopropyl)methylamine--.

At column 5, lines 59 and 60, delete "3,3'-dichloro-4,4'-diaminodipheryl-methane" and insert --3,3'-dichloro-4,4'-diaminodiphenylmethane--.

At column 6, line 18, delete "quiniiol" and insert --quinitol--.

UNITED STATES PATENT AND TRADEMARK OFFICE
CERTIFICATE OF CORRECTION

PATENT NO. : 5,099,058
DATED : March 24, 1992
INVENTOR(S) : Josef Sanders and Dieter Dieterich It is certified that error appears in the above-identified patent and that said Letters Patent is hereby corrected as shown below:

At column 6, lines 44 and 45, delete "polyhydrazocicarbonamides" to insert --polyhydrazodicarbonamides--.

At column 12, line 11, after "such a" and before "quantity", delete "o";

At column 12, line 21, after "at about 10°C to about", insert --100°C--.

At column 13, line 65, after "carried out at 10° to", insert --100°C--.

At column 16, line 24, delete "(80 g, mole)" and insert --(80 g, 2 mole)--.

In Claim 26, at column 22, line 66, delete "7 to carbon atoms" and insert --7 to 15 carbon atoms--.

Signed and Sealed this

Ninth Day of November, 1993

Attest:

BRUCE LEHMAN

Attesting Officer    Commissioner of Patents and Trademarks